United States Patent [19]

Masters

[11] Patent Number: 5,911,917
[45] Date of Patent: Jun. 15, 1999

[54] PRESERVED CELLULAR STRUCTURES

[76] Inventor: Thomas R. Masters, 6601 Prairie Rim Rd., Lincoln, Nebr. 68526

[21] Appl. No.: 08/915,859

[22] Filed: Aug. 21, 1997

Related U.S. Application Data

[63] Continuation-in-part of application No. 08/540,941, Oct. 11, 1995, abandoned, which is a continuation of application No. 08/218,054, Mar. 25, 1994, abandoned, which is a continuation-in-part of application No. 07/904,171, Jun. 24, 1992, Pat. No. 5,300,540, which is a continuation-in-part of application No. 07/578,806, Sep. 4, 1990, abandoned.

[51] Int. Cl.⁶ .......................... C09K 15/32; C09K 15/16; A01N 3/00; A41G 1/00

[52] U.S. Cl. ..................... 252/400.1; 252/400.2; 252/400.4; 252/400.52; 252/400.53; 252/401; 504/114; 504/115; 428/17; 428/23; 428/24; 34/299; 34/287

[58] Field of Search ............... 252/400.1, 400.2, 252/400.4, 400.52, 400.53, 401; 504/114, 115; 428/17, 23, 24; 34/299, 287

[56] References Cited

U.S. PATENT DOCUMENTS

| | | | |
|---|---|---|---|
| 2,203,274 | 6/1940 | Anderson | 504/115 X |
| 2,567,929 | 9/1951 | Fessenden | 504/115 X |
| 2,658,836 | 11/1953 | Fessenden | 427/4 |
| 2,907,722 | 10/1959 | Staicopoulos | 524/513 |
| 2,923,095 | 2/1960 | Magimel-Pelonnier | 427/4 |
| 2,971,292 | 2/1961 | Malecki | 504/115 X |
| 3,122,432 | 2/1964 | Biggs | 504/114 |
| 3,134,661 | 5/1964 | Sheppard | 504/115 |
| 3,157,964 | 11/1964 | Ferguson | 504/114 X |
| 3,160,985 | 12/1964 | Ferguson | 504/114 X |
| 3,220,823 | 11/1965 | Mihara | 504/114 X |
| 3,287,104 | 11/1966 | Biggs | 504/115 |
| 3,320,046 | 5/1967 | Siegel | 71/2.4 |
| 3,362,920 | 1/1968 | Anagnostou et al. | 524/37 |
| 3,545,129 | 12/1970 | Schreiber et al. | 427/4 |
| 3,656,949 | 4/1972 | Honjo et al. | 96/15 |
| 3,818,105 | 6/1974 | Coopersmith et al. | 428/358 |
| 3,835,550 | 9/1974 | Kaneko | 34/5 |
| 3,861,053 | 1/1975 | Rovetti | 34/9 |
| 3,865,569 | 2/1975 | Parups et al. | 71/68 |
| 3,874,871 | 4/1975 | Sy et al. | 504/115 |
| 3,895,140 | 7/1975 | Sheldon et al. | 428/22 |
| 3,950,892 | 4/1976 | Simkin | 47/58 |
| 3,966,667 | 6/1976 | Sullivan et al. | 524/476 |
| 4,049,837 | 9/1977 | Freebairn | 427/4 |
| 4,071,489 | 1/1978 | Emmons et al. | 523/503 |
| 4,092,145 | 5/1978 | Willard, Sr. | 504/115 |
| 4,121,944 | 10/1978 | VanLandingham | 106/213 |
| 4,225,679 | 9/1980 | Pilato | 504/115 |
| 4,256,773 | 3/1981 | Itoga et al. | 504/114 X |
| 4,272,571 | 6/1981 | Romero-Sierra et al. | 428/24 |
| 4,278,715 | 7/1981 | Romero-Sierra et al. | 428/22 |
| 4,287,222 | 9/1981 | Robinson | 427/4 |
| 4,312,134 | 1/1982 | Strausser | 34/5 |
| 4,328,256 | 5/1982 | Romero-Sierra et al. | 427/4 |
| 4,349,459 | 9/1982 | Romero-Sierra et al. | 504/115 Y |
| 4,349,580 | 9/1982 | Romero-Sierra et al. | 427/4 |
| 4,461,871 | 7/1984 | Kometani et al. | 523/437 |
| 4,561,995 | 12/1985 | Fenn | 252/194 |
| 4,651,467 | 3/1987 | Tapia et al. | 47/58 |
| 4,664,956 | 5/1987 | Dokkestul et al. | 428/22 |
| 4,783,351 | 11/1988 | Baker | 427/4 |
| 4,808,447 | 2/1989 | Baker | 428/17 |
| 4,985,061 | 1/1991 | Hughes | 504/115 |
| 5,039,731 | 8/1991 | Warren et al. | 524/507 |
| 5,080,707 | 1/1992 | Ide et al. | 504/115 |
| 5,112,380 | 5/1992 | Yamamoto et al. | 504/115 X |
| 5,284,818 | 2/1994 | Shafer | 504/115 |
| 5,321,006 | 6/1994 | Mookherjee et al. | 512/5 |
| 5,656,343 | 8/1997 | Baker | 428/17 |

*Primary Examiner*—C. H. Kelly
*Attorney, Agent, or Firm*—Koley, Jessen, Daubman & Rupiper, P.C.; Mark D. Frederiksen

[57] ABSTRACT

A process for preserving cellular structures includes the steps of pre-treating the structures with an aqueous polymeric water solution, drying the structures and then post-treating the structures with an organic solvent, non-water-base solution. Once the structure has been treated with the pre-treatment solution, the specimen is allowed to sit for a predetermined period of time in order for the active ingredients of the solution to penetrate the surface area of the specimen. The specimen is then preferably freeze-dried. The solution may also be applied to the cellular material by drawing it systemically through the material.

14 Claims, No Drawings

PRESERVED CELLULAR STRUCTURES

CROSS-REFERENCE TO RELATED APPLICATION

This is a continuation-in-part application of continuation application Ser. No. 08/540,941 filed Oct. 11, 1995 now abandoned which is a continuation of Ser. No. 08/218,054 filed Mar. 25, 1994, now abandoned, which is a continuation-in-part of Ser. No. 07/904,171 filed Jun. 24, 1992 which issued as U.S. Pat. No. 5,300,540, which is a continuation-in-part of Ser. No. 07/578,806 filed Sep. 4, 1990, now abandoned.

TECHNICAL FIELD

The present invention relates generally to the preservation of flowers and other cellular structures, and more particularly to a process and novel composition of matter for the preservation of cellular structures after the structures have been dried.

BACKGROUND OF THE INVENTION

The preservation of flowers and other naturally occurring plant materials, as well as non-living animal tissues has been practiced for many years, and many processes for such preservation have been described in literature. The main problem with the processes conventional in the art is that the preservation process has usually affected the appearance, shape and/or texture of the cellular structure. Thus, the natural colors of flowers tend to fade, and the cellular structures may be brittle, fragile and highly susceptible to damage due to extreme temperature or humidity.

It is therefore a general object of the present invention to provide a process and composition of matter for the preservation of cellular structures which will result in natural coloring, flexibility and freshness characteristics for relatively long periods of time after the preservation process.

Another object of the invention is to provide an economical and affordable method and process of preserving cellular material not previously known.

Another object of the present invention is to provide a freeze-drying process which significantly enhances the preservation of the cellular structure preserved thereby.

These and other objects will be apparent to those skilled in the art.

SUMMARY OF THE INVENTION

The process for preserving cellular structures of the present invention includes the steps of pre-treating the structures with a polymeric water solution, drying the structures and then post-treating the structures with a solvent-based solution. Once the structure has been treated with the pre-treatment solution, the specimen is allowed to sit for a predetermined period of time in order for the active ingredients of the solution to penetrate the surface area of the specimen. The specimen is then quick frozen in the specimen chamber of a freeze dryer to lock the water into an ice matrix. At the same time, silica sand is frozen, and inserted within the specimen chamber of the freeze dryer to completely cover the specimens. The specimens are then placed in a high vacuum to draw off the water and dry the specimens. The specimens are maintained at a temperature of about –10° F. to 30° F. for two to ten days while under vacuum. Once the specimens are dry, the specimen chamber temperature is allowed to climb to room temperature, thereby enhancing sublimation of any remaining water vapor. The specimens are removed from the freeze dryer into a controlled environment with a humidity of 50 percent or lower. The specimens are then treated with a non-water-based post-treatment solution to form a barrier coat on the finished product.

DESCRIPTION OF THE PREFERRED EMBODIMENTS

The basic concept of the present invention calls for pre-treatment of flowers and other natural cell structures such as fruit, vegetable and other plants, as well as the cellular structure of non-living animal tissues, with a unique polymeric water solution. A freeze-drying process is then preferably utilized to dry the cellular structures. A post-treatment with a solvent-based solution completes the process to produce preserved cellular material with natural structural integrity and durability, and with little sensitivity to normal variations of temperature, humidity and light. The preservation process enables the user to produce a viable, inexpensive and well-preserved product. The pre-treatment solution is a water-based solution so as to prevent damage to the freeze dryer during the freeze-drying process. It is for this reason that a standard petroleum-based solvent solution for pre-treatment is unacceptable. The pre-treatment solution preferably includes: (a) at least one monohydric alcohol; (b) at least one component selected from a group comprised of lower carbon- chained carboxylic acids; (c) at least one of a group comprised of antioxidants; (d) at least one of a group of sequestering agents; (e) at least one of a group comprised of humectants; (f) at least one from a group of organic acids, namely, a group of organic acids that easily disassociate in water, giving up a hydrogen ion to thereby lower the pH with a $pK_1$ range from 2.0 to 5.5 (g) amines for use as buffers; (h) transitional metallic salts; and (i) at least one component from the groups of sulfate, phosphates, nitrates and chlorides with stable equilibriums in the pH range from 1.0 to 7.4.

In the preferred embodiment, the composition includes sequestering or chelating agents selected from the group consisting of ethylene diamine tetracetic acid and phosphoric acid, and mordant reagents which are preferably metallic salts selected from the group consisting of salts of ammoniums, phosphates, sulfates, nitrates and chlorides.

Preferably, the solution also includes the following, which may also provide multiple functions in the composition: (1) a water-soluble film forming agent, such as starches, modified starches and cellulosic thickeners, such as carboxymethyl cellulose; (2) water suspended thermoplastic polymers, such as acrylics; (3) modified hydroxy-containing polyalcohols; (4) plasticizers such as polyols, substituted water-soluble sulfonated vegetable oils and carbowaxes; (5) synthetic and natural vegetable gums; (6) water-soluble films catalyzed with metallic salts, including: ammonium salts and other chlorinated, halogenated salts; (7) cross-linkers, including glyoxal acetal, aldehyde; (8) functional resins such as melamine type reactants; (9) dispersible waxes and pseudo-waxes; (10) emulsifying agents from the group comprising methoxylated, ethoxylated, vegetable oils, and esters and alcohols; (11) borax and boric acid derived complexes for use as catalysts; and (12) biological preservatives.

The amount of each chemical required depends upon the type of cellular material being treated. Furthermore, the chemical formulation must take into consideration the material treated, the ease of formulation, the process of application, the toxicity to the environment, and the cost of formulated materials as well as the overall final market value of the finished product.

The preferred embodiment of the invention includes the following components and ranges of each component:

0.1 to 3 g EDTA acid
3 to 20 ml ammonium lauryl sulfate
0.1 to 2 g acetylsalicylic acid
0.1 to 5 g copper sulfate
5 to 75 g citric acid
25 to 200 g synthetic vegetable gum
10 to 500 ml blended alcohol
1 to 35 g isoascorbic acid
800 to 1600 ml water
100 to 750 ml sorbitol
25 to 250 ml glycerine
25 to 200 ml ethoxylated alcohol
25 to 300 ml ethoxylated triglyceride
15 to 100 g glycerol monostearate
5 to 75 ml glyoxal
0.5 to 2 g PABA
1 to 20 g aluminum sulfate
10 to 150 g ammonium chloride
20 to 300 ml phosphate ester
1 to 35 g boric acid
25 to 200 g benzoic acid
50 to 300 ml ethoxylated sorbitol
10 to 150 ml ethoxylated sorbitan ester
5 to 50 g ethoxylated stearic acid
25 to 200 ml ethoxylated alkyl phenol
1 to 25 g sodium metabisulfite
5 to 100 g acrylate resin
1 to 5 g nickel chloride
1 to 10 9 potassium chloride
1 to 50 g sodium hypochlorite
1 to 55 g zinc sulfate The pre-treatment solution described above is applied to all surfaces of the cellular material specimen to be preserved. The application may be sprayed as a fine mist, or the specimen may be dipped or soaked in the solution, so as to cover all surfaces of the specimen. Alternatively, the solution may be drawn systemically throughout the material until the material is saturated. The specimen is then placed on a tray, rack or suitable receptacle and allowed to sit for a predetermined amount of time in order for the active ingredients of the solution to penetrate the surface area of the specimen. The specimen tray is then loaded into the specimen chamber of a freeze dryer to freeze the specimens. It is preferable that the specimen chamber temperature be $-10°$ F. or lower, in order to achieve a quick freeze of the specimen with minimal changes in the specimen condition. While a very lower temperature is the preferred method for preloading the specimen, acceptable results may be achieved with specimen chamber temperatures as high as 34° to 45° F. during loading of the specimens. Once the loading is completed, the temperature would then be lowered to $-10°$ F. or lower.

The specimens are maintained within the specimen chamber at a temperature between $-10°$ and $-30°$ F. for a period of 3 to 24 hours before the chamber is placed in a vacuum. The step of freezing the specimen will lock the water into an ice matrix, and thereby minimize shrinking and distortion that would otherwise occur if liquid water were present when the vacuum is pulled on the system.

At the same time, a quantity of silica sand is also frozen to substantially the same temperature as the specimens. The silica sand is then inserted into the specimen chamber of the freeze dryer, with the specimens laid atop a bed of frozen silica sand, and then a layer of silica sand poured over the top of the specimens. In this way, silica sand contacts substantially the entire surface area of the specimens.

It can be seen that the main reason for a water-based polymer complex in the pre-treatment solution is because petroleum based solvents would damage the condensation chambers of commercially available freeze dryers, contaminating the vacuum pump oil and thus damaging the entire vacuum system. In the freeze-drying process, water within the cell structure of the specimen is frozen and will sublimate in a high vacuum. The water vapor is collected in a condensation chamber which may be defrosted periodically without disturbing the specimen chamber. Thus, water is continuously removed from the specimen chamber so as to dry the specimens, in a process which is hereinafter referred to as "vacuum dehydration".

Preferably, a high vacuum (25 to 100 microns mercury) is necessary in order to dry the frozen specimens efficiently. Gradually, the specimen chamber temperature is then increased to allow for complete sublimation of the water in the specimen. For example, the standard temperature range of the specimen chamber for most flowers (such as roses, carnations, pansies, irises, narcissus, asters, etc.) is $-10°$ F. to $+30°$ F. over a two to ten day period. Thick petaled or stemmed items (such as orchids, ginger, heliconia, protea, banksia, strelitzia, oriental lilies, etc.) require a longer period of time to achieve a complete sublimation of the water, at a temperature range from $-10°$ F. to $+20°$ F. or higher. A load of fruits and vegetables will dry in the $-10°$ to $+30°$ F. temperature range in four to sixteen days depending upon the water content and density of the specimens, the amount of specimens, as well as the overall efficiency of the freeze dryer itself. The use of silica sand covering the specimens enhances the transfer of liquid from the specimens to the silica, with a more uniform migration of heat and therefore a more uniform dehydration of the specimens.

As noted above, the condensation chamber is defrosted as necessary to maintain operational efficiency of the freeze dryer. The specimens within the freeze dryer are considered dry when ice does not form in the condensation chamber over a 4 to 24 hour period, the vacuum reading is sustained between 10 to 15 microns and the temperature is in the range of 30° F. and above. At this point, the specimen chamber refrigeration compressor may be turned off, allowing the specimen chamber temperature to climb to 60° to 80° F. over a 4 to 24 hour period. This increase in temperature will drive the remaining ice in the specimen into water vapor and complete the drying process.

While the specimens which are freeze dried according to the above vacuum dehydration process, and which have been pre-treated utilizing the solution described above, will possess greater durability and color intensity than untreated specimens, they are still susceptible to reabsorption of water vapor within a relatively short period of time. In order to sustain the finished product in a durable, flexible and resilient form and so as to retain natural life-like characteristics and prevent premature disintegration, fading and excessive reabsorption of water, a process of post-treatment of the specimens is utilized.

It is important that the specimens be unloaded from the freeze dryer into a controlled environment, with a humidity level of 50 percent or lower, and a temperature of 70° F. or higher. The specimens are sprayed, dipped or soaked in a post-treatment solution, in a fashion to cover all surface areas of the specimens. This controlled environment will insure that the solvents in the post-treatment solution will evaporate quickly, usually within 8 to 24 hours, without absorbing water vapor during the process. Two or more coatings of the solution may be applied, depending upon the quality and thickness of the barrier coat desired on the finished product.

In general, the post treatment solution is an organic solvent, non-water-base solution which includes a water-resistant, film-forming polymeric resin. Elastomeric resins or a blend of elastomeric resins with thermoplastic resin and thermosetting resins yield excellent results. Elastomeric resins selected from the group of chlorinated sulfonated polyethylene resins used as the primary resin have been found to yield the best results.

Other preferable additions to this solution include: (1) a water resistant thermoplastic resin selected from the group of solvated chlorinated polyolefins and (2) a thermoset plastic selected from the group of alkyloxysilane resins.

This post-treatment solution assists in sustaining the desired structural integrity and color of the specimens after freeze-drying, and helps reduce deterioration.

Preferably, the post treatment solution also includes: (1) ethanol; (2) C-1 to C-6 carbon chain alcohol blends; (3) thermosetting resin such as alkyloxysilane resin in petroleum solvent; (4) at least one of a group comprised of antioxidants, such as butylated hydroxyanisole, butylated hydroxytoluene, and propyl gallate; (5) at least one of the group comprised of polyols, derived polyols, and esters; (6) plasticizers, such as paraffin waxes and modified waxes; (7) polymerics, such as polyethylene glycols; (8) waxes; (9) phthalate types; (10) high molecular weight oils; (11) emulsified wax;(12) emulsifiers including polyoxyethylene sorbitan monooleate and other non-ionic emulsifiers such as polyoxyethylene ethers of octyl or nonyl phenol, ethoxylated alcohols, and similar surfactants; (13) catalysts, such as borax or boric acid; (14) salts; (15) preservatives, such as benzoic acid, benzoate salts, and their derivatives; (16) ultraviolet absorbers such as hydroxyphenyl benzotriazoles; (17) radical scavengers such as hindered tertiary amines; (18) colorants; and (19) fragrances, if needed.

Whereas the invention has been described in connection with the preferred embodiments thereof, it will be understood that many modifications, substitutions and additions may be made which are within the intended broad scope of the appended claims. There has therefore been described a freeze-drying process with pre-treatment and post-treatment of cellular material specimens which accomplishes at least all of the above-stated objects.

I claim:

1. A process for preserving the nature colors and structural integrity of flowers, plants, vegetables and other natural cellular material, comprising the steps of:
   applying an aqueous solution to the entire surface of said cellular material, the aqueous solution consisting essentially of:
   at least one lower carboxylic acid having a carbon chain length from $C_1$ and $C_{10}$;
   a transitional metallic salt selected from the group consisting of phosphates, sulfates and nitrates;
   a halogenated salt selected from the group consisting of chlorides;
   a buffer selected from the group consisting of amines and phosphoric acid, which operates in the pH range from 1.0 to 7.4; and
   a mordant reagent; and freeze-drying the cellular material to substantially eliminate the water in the cellular material.

2. The process of claim 1, wherein the step of freeze-drying includes the steps of:
   reducing the temperature of the cellular material below freezing; and
   vacuum dehydrating the cellular material until a predetermined amount of water has been removed from the cellular material.

3. The process of claim 2, wherein the step of vacuum dehydrating the cellular material further includes the steps of:
   reducing the temperature of a quantity of silica sand to substantially the same reduced
   temperature of the cellular material;
   placing the cellular material in the reduced-temperature silica sand so as to substantially cover the cellular material with the silica sand; and thence
   placing the cellular material and silica sand under a vacuum until a predetermined amount of water has been removed from the cellular material.

4. The process of claim 1, wherein said aqueous solution further comprises an antioxidant selected from the group consisting of butylated hydroxyanisole, butylated hydroxytoluene and propyl gallate.

5. The process of claim 1, wherein said aqueous solution further comprises:
   cross-linkers selected from the group consisting of melamines, glyoxal, acetal and aldehydes;
   a catalyst selected from the group consisting of borates, boric acid and borate complexes; and
   wherein said metallic salts are selected from the group consisting of stannous chloride nickel chloride, magnesium sulfate, aluminum sulfate, copper sulfate and zinc sulfate.

6. The process of claim 1, wherein said aqueous solution further comprises sequestering or chelating agents selected from the group consisting of ethylene diamine tetracetic acid and phosphoric acid.

7. The process of claim 1, wherein said mordant reagents are metallic salts selected from the group consisting of salts of ammoniums, phosphates, sulfates, nitrates and chlorides.

8. The process of claim 1, wherein said aqueous solution further comprises a preservative selected from the group consisting of PABA, benzoic acid, sodium benzoate and quaternary ammonium compounds.

9. The process of claim 1, wherein said buffer is selected from the group consisting of amines.

10. The process of claim 1, wherein said aqueous solution further comprises a humectant.

11. The process of claim 10, wherein said humectant is selected from the group consisting of polyols, starches and water-soluble plasticizers.

12. The process of claim 1, wherein said aqueous solution further comprises a monohydric alcohol selected from the group consisting of C-1 to C-5 carbon chain alcohols.

13. The process of claim 1, wherein said aqueous solution further comprises a di- and tri-hydric alcohol.

14. The process of claim 1, wherein said aqueous solution further comprises plasticizers selected from the group of emulsified waxes and high molecular weight oil emulsion, non-ionic emulsifiers, and surfactants.

* * * * *